United States Patent [19]

Egli et al.

[11] Patent Number: 5,132,411
[45] Date of Patent: Jul. 21, 1992

[54] AZO COMPOUNDS HAVING 2,4-DISUBSTITUTED-3-HALOTHIENYL-5-DIAZO COMPONENT RADICALS, DYEING PROCESSES THEREWITH AND SUBSTRATES DYED THEREWITH

[75] Inventors: Robert Egli, Therwil; Beat Henzi, Basel, both of Switzerland

[73] Assignee: Sandoz Ltd., Basel, Switzerland

[21] Appl. No.: 495,517

[22] Filed: Mar. 19, 1990

Related U.S. Application Data

[63] Continuation-in-part of Ser. No. 157,441, Feb. 17, 1988, abandoned, which is a continuation of Ser. No. 920,818, Oct. 17, 1986, abandoned, which is a continuation of Ser. No. 771,277, Aug. 30, 1985, abandoned.

[30] Foreign Application Priority Data

Aug. 30, 1984 [DE] Fed. Rep. of Germany ....... 3431846

[51] Int. Cl.$^5$ .................... C09B 29/033; C09B 29/09; C09B 29/36; D06P 1/04
[52] U.S. Cl. ................................. 534/753; 534/738; 534/765; 534/768; 534/776; 534/778; 534/779; 549/68
[58] Field of Search ............... 534/753, 768, 630, 765, 534/776, 778, 779, 738; 549/68

[56] References Cited

U.S. PATENT DOCUMENTS

| | | | |
|---|---|---|---|
| 4,264,495 | 4/1981 | Maher et al. | 534/768 X |
| 4,307,015 | 12/1981 | Koerte | 534/768 |
| 4,395,544 | 7/1983 | Egli | 534/768 |
| 4,400,318 | 8/1983 | Weaver et al. | 534/768 |
| 4,439,362 | 3/1984 | Koerte | 534/768 |
| 4,505,857 | 3/1985 | Egli | 534/768 X |
| 4,507,407 | 3/1985 | Kluger | 534/753 X |
| 4,814,465 | 3/1989 | Etzbach | 549/68 X |
| 4,904,777 | 2/1990 | Etzbach et al. | 534/738 |
| 4,952,681 | 8/1990 | Hansen et al. | 534/766 |

FOREIGN PATENT DOCUMENTS

| | | | |
|---|---|---|---|
| 2818101 | 11/1978 | Fed. Rep. of Germany | 534/768 |
| 49-42376 | 3/1984 | Japan | 534/768 |
| 59-204658 | 11/1984 | Japan . | |
| 1434654 | 5/1976 | United Kingdom | 534/630 |
| 1436176 | 5/1976 | United Kingdom . | |

OTHER PUBLICATIONS

Wiesenfeldt et al, Chemical Abstracts, vol. 114, No. 163991k (1991).
Research Disclosure, No. 19826, pp. 425-427 (Oct., 1980).

*Primary Examiner*—Mary C. Lee
*Assistant Examiner*—Fiona T. Powers

*Attorney, Agent, or Firm*—Gerald D. Sharkin; Richard E. Vila; Melvyn M. Kassenoff

[57] ABSTRACT

Compounds of the formula

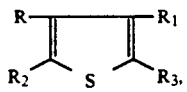

wherein
R is halo,
$R_1$ is cyano; ($C_{1-6}$alkoxy)carbonyl; ($C_{3-6}$alkenyl)oxycarbonyl; $C_{1-4}$alkylsulfonyl; phenylsulfonyl; ($C_{1-4}$alkyl)carbonyl; benzoyl; carbamoyl; ($C_{1-4}$alkyl)carbamoyl; N,N-di-($C_{1-4}$alkyl)carbamoyl; phenylcarbamoyl; benzyloxycarbonyl; or ($C_{1-6}$alkoxy)carbonyl, ($C_{3-6}$alkenyl)oxycarbonyl, $C_{1-4}$alkylsulfonyl, phenylsulfonyl or ($C_{1-4}$alkyl)carbamoyl substituted by one or two substituents independently selected from chloro, bromo, $C_{1-4}$alkyl, $C_{1-4}$alkoxy, hydroxy, cyano and acyl, and
$R_2$ is formyl, cyano, —CH=C($R_4$)$_2$ or —CH=N—OH, wherein (1) each $R_4$ is independently cyano; ($C_{1-6}$alkoxy)carbonyl; ($C_{3-6}$alkenyl)oxycarbonyl; ($C_{3-6}$alkynyl)oxycarbonyl; or ($C_{1-6}$alkoxy)carbonyl, ($C_{3-6}$alkenyl)oxycarbonyl or ($C_{3-6}$alkynyl)oxycarbonyl substituted by one or two substituents independently selected from chloro, bromo, $C_{1-4}$alkyl, $C_{1-4}$alkoxy, hydroxy, cyano and acyl,
(2) one $R_4$ is cyano and the other is benzoyl or benzoyl monosubstituted by ($C_{1-4}$alkoxy)carbonyl, $C_{1-4}$alkylsulfonyl, phyenylsulfonyl, carbamoyl, ($C_{1-4}$alkyl)carbamoyl, phenylcarbamoyl or ($C_{1-4}$alkoxy)carbonyl, $C_{1-4}$alkylsulfonyl, phenylsulfonyl or ($C_{1-4}$alkyl)carbamoyl substituted by one or two substituents independently selected from chloro, bromo, $C_{1-4}$alkyl, $C_{1-4}$alkoxy, hydroxy, cyano and acyl,
(3) one $R_4$ is hydrogen and the other is benzoyl; benzoyl monosubstituted by ($C_{1-2}$alkoxy)carbonyl, halo, $C_{1-4}$alkyl, nitro or ($C_{1-2}$alkoxy)carbonyl substituted by one or two substitutents independently selected from chloro, bromo, $C_{1-4}$alkyl, $C_{1-4}$alkoxy, hydroxy, cyano and acyl; ($C_{1-4}$alkyl)carbonyl or ($C_{3-6}$alkenyl)carbonyl or
(4) one $R_4$ is nitro and the other is hydrogen, methyl or ethyl, and
$R_3$ is amino or —N=N—K, wherein K is a coupling component radical.

The compounds wherein $R_3$ is —N=N—K are useful as disperse dyes and those wherein it is amino are useful as intermediates in the synthesis of those wherein it is —N=N—K.

19 Claims, No Drawings

AZO COMPOUNDS HAVING 2,4-DISUBSTITUTED-3-HALOTHIENYL-5-DIAZO COMPONENT RADICALS, DYEING PROCESSES THEREWITH AND SUBSTRATES DYED THEREWITH

This is a continuation-in-part of application Ser. No. 07/157,441, filed Feb. 17, 1988 and now abandoned which is a continuation of application Ser. No. 06/920,818, filed Oct. 17, 1986 and now abandoned, which is a continuation of application Ser. No. 06/771,277, filed Aug. 30, 1985 and now abandoned.

The invention relates to thiophene ring-containing compounds useful as disperse dyes or for preparing disperse dyes.

According to the invention there is provided compounds of formula I

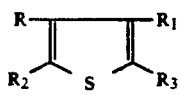

in which
R is halogen,
$R_1$ is cyano, $C_{1-6}$alkoxycarbonyl, $C_{3-6}$alkenyloxycarbonyl, aminocarbonyl, $C_{1-4}$alkylsulphonyl, phenylsulphonyl, $C_{1-4}$alkyl- or phenyl-carbonyl, phenyl-, mono-$C_{1-4}$alkyl- or di-$C_{1-4}$alkyl-aminocarbonyl or benzyloxycarbonyl;
$R_2$ is formyl, cyano, —CH═C(R$_4$)$_2$ or —CH═N—OH; and
$R_3$ is —N═N—K or —NH$_2$; wherein K is a coupling component radical; each $R_4$ independently is cyano, $C_{1-6}$alkoxycarbonyl, $C_{3-6}$alkenyloxycarbonyl or $C_{3-6}$alkynyloxycarbonyl; or one $R_4$ is cyano and the other $R_4$ is benzoyl unsubstituted or monosubstituted by $C_{1-4}$alkoxycarbonyl, $C_{1-4}$alkylsulphonyl, phenylsulphonyl or aminocarbonyl unsubstituted or monosubstituted by $C_{1-4}$alkyl or phenyl; or one $R_4$ is hydrogen and the other $R_4$ is benzoyl unsubstituted or monosubstituted by $C_{1-2}$alkoxycarbonyl, halogen, $C_{1-4}$alkyl or —NO$_2$; $C_{1-4}$alkylcarbonyl or $C_{3-6}$alkenylcarbonyl; or one $R_4$ is nitro and the other $R_4$ is hydrogen, methyl or ethyl.

In $R_1$ and $R_4$ any alkoxycarbonyl, alkenyloxycarbonyl, phenoxyalkylcarbonyl, phenoxycarbonyl, alkylaminocarbonyl, alkylsulphonyl, phenylsulphonyl or alkynyloxycarbonyl is unsubstituted or substituted by 1 or 2 substituents independently selected from Cl, Br, $C_{1-4}$alkyl, $C_{1-4}$alkoxy, hydroxy, cyano and acyl, for example

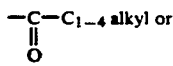

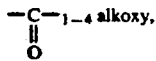

preferably not more than 1, unless indicated to the contrary. Preferably, any such group is unsubstituted, unless indicated to the contrary.

For the avoidance of doubt, any group capable of being linear or branched is linear or branched unless indicated to the contrary.

In this specification, halogen is chloro or bromo, more preferably chloro.
Preferably any alkyl group is $C_{1-2}$alkyl.
Preferably any alkenyl group is $C_{3-4}$alkenyl.
Preferably any alkoxy group is $C_{1-2}$alkoxy.
Preferably any alkynyl group is $C_{3-4}$alkynyl.

In the compounds of formula I preferably $R_1$ is $R_1'$, where $R_1'$ is cyano, $C_{1-4}$alkoxycarbonyl, $C_{3-4}$alkenyloxycarbonyl, $C_{1-4}$alkoxy- $C_{2-4}$alkoxycarbonyl, benzyloxycarbonyl, monoC$_{1-4}$alkylaminocarbonyl, $C_{1-4}$alkylsulphonyl or phenylsulphonyl. More preferably $R_1$ is $R_1''$, where $R_1''$ is cyano, $C_{1-2}$alkoxycarbonyl, monoC$_{1-2}$alkylaminocarbonyl, $C_{1-2}$alkylsulphonyl or phenylsulphonyl. Most preferably $R_1$ is $R_1'''$, where $R_1'''$ is cyano or $C_{1-2}$alkoxycarbonyl.

$R_2$ is preferably $R_2'$, where $R_2'$ is formyl, cyano, —CH═C(R$_4'$)$_2$, where each $R_4'$ independently is cyano, $C_{1-6}$alkoxycarbonyl, $C_{3-6}$alkenyloxycarbonyl or (2-$C_{1-4}$alkoxyethoxy)carbonyl or one $R_4'$ is nitro and the other $R_4'$ is hydrogen. More preferably $R_2$ is $R_2''$, where $R_2''$ is formyl or cyano. Most preferably $R_2$ is formyl.

$R_4$ is preferably $R_4'$ defined above, more preferably $R_4''$, where one $R_4''$ is cyano and the other $R_4''$ is $C_{1-6}$alkoxycarbonyl.

K is preferably K', where K' is a coupling component radical of the aniline, α-naphthylamine, pyrazole, aminopyrazole, indole, tetrahydroquinoline, thiazole, phenol, naphthol, benzomorpholine or pyridine series. More preferably K is K'', where K'' is a group of formula a

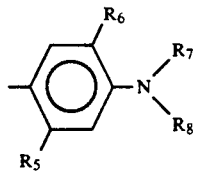

in which
$R_5$ is hydrogen; $C_{1-2}$alkyl; $C_{1-2}$alkoxy; formylamino; $C_{1-4}$alkylcarbonylamino in which the alkyl group is unsubstituted or monosubstituted by hydroxy, chloro, bromo, $C_{1-4}$alkoxy, phenyl, phenoxy, benzyloxy, $C_{1-2}$alkylcarbonyloxy or $C_{1-2}$alkoxycarbonyl; benzoylamino (preferably by other than $C_{1-2}$alkylcarbonyloxy); acryloylamino; aminocarbonylamino; $C_{1-4}$alkylaminocarbonylamino; $C_{1-4}$alkoxycarbonylamino in which the alkoxy group is unsubstituted or monosubstituted by $C_{1-2}$alkoxy or phenyl; $C_{1-2}$alkyl- or phenylsulphonylamino; di-($C_{1-2}$alkyl)aminosulphonylamino; fluoro; chloro or bromo;

$R_6$ is hydrogen fluoro, chloro, bromo, $C_{1-2}$alkyl, $C_{1-4}$alkoxy or $C_{1-2}$alkoxyethoxy, provided that when $R_5$ is fluoro, chloro or bromo, $R_6$ is other than fluoro, chloro and bromo;

$R_7$ is hydrogen; $C_{1-10}$alkyl; $C_{2-10}$alkyl monosubstituted by chloro, bromo, hydroxy, cyclohexyl, -SCN, cyano, $C_{1-4}$alkylcarbonyl, $C_{1-4}$alkoxycarbonyl, formyloxy, $C_{1-10}$alkylcarbonyloxy, chloro- or bromo- $C_{1-3}$alkylcarbonyloxy, $C_{1-10}$alkoxycarbonyloxy, $C_{1-2}$alkoxyethoxycarbonyloxy, $C_{3-4}$alkenyloxycarbonyl, chloro- or bromo-allyloxycarbonyl, $C_{3-4}$alkenyloxy, chloro- or bromo- allyloxy, $C_{3-4}$alkynyloxy, benzoyloxy, benzyloxy, $C_{1-10}$alkoxy, phenyl, phenoxy, phenyl($C_{1-4}$alkoxy), ($C_{1-2}$alkoxy)ethoxycarbonyl or benzyloxycarbonyl (preferably by other than benzyloxy); $C_{2-10}$alkyl disubstituted by chloro, bromo, hydroxy, formyloxy, ($C_{1-4}$alkyl)carbonyloxy, chloro- or bromo-($C_{1-3}$alkyl)-carbonyloxy, ($C_{1-4}$alkoxy)carbonyloxy, ($C_{1-2}$alkoxy)ethoxycarbonyloxy, chloro- or bromo-allyloxycarbonyl, $C_{3-4}$alkynyloxy or ($C_{1-2}$alkoxy)ethoxycarbonyl; $C_{1-4}$alkoxy$C_{2-6}$alkyl in which the alkyl moiety of the alkoxy is monosubstituted by chloro, bromo, cyano, $C_{1-4}$alkoxy, alkoxy, $C_{1-4}$alkoxycarbonyl, $C_{1-4}$alkoxycarbonyloxy or $C_{1-4}$alkylcarbonyloxy; β-($C_{1-4}$alkoxycarbonylmethoxycarbonyl)ethyl; $C_{3-4}$alkenyl, unsubstituted or monosubstituted by phenyl, chloro or bromo; propynyl; $C_{5-7}$cycloalkyl; cyclohexyl mono-, di- or tri-substituted by methyl; phenyl, unsubstituted or monosubstituted by chloro, bromo, nitro or $C_{1-4}$alkoxy or mono-, di- or tri-substituted by methyl; or β-hydroxypropyl monosubstituted by γ-$C_{1-4}$alkoxy, γ-$C_{3-4}$alkenyloxy or γ-phenoxy; and $R_8$ is hydrogen; $C_{1-10}$alkyl; $C_{2-10}$alkyl monosubstituted by chloro, bromo, hydroxy, cyano, -SCN, $C_{1-10}$alkylcarbonyl, $C_{1-10}$alkoxycarbonyl, formyloxy, $C_{1-10}$alkylcarbonyloxy, chloro- or bromo-$C_{1-4}$alkylcarbonyloxy, $C_{1-10}$alkoxycarbonyloxy, $C_{1-2}$alkoxyethoxycarbonyloxy, $C_{3-4}$alkenyloxycarbonyl, chloro- or bromo-allyloxycarbonyl, $C_{3-4}$alkenyloxy, chloro- or bromo-allyloxy, $C_{3-4}$alkynyloxy, benzoyloxy, benzyloxy, $C_{1-10}$alkoxy, phenyl, phenoxy, phenyl $C_{1-4}$alkoxy, aminocarbonyl, mono-$C_{1-4}$alkyl- or di-($C_{1-4}$alkyl)aminocarbonyl, mono-$C_{1-4}$alkyl- or di-($C_{1-4}$alkyl)aminocarbonyloxy, phenylaminocarbonyl, phenylaminocarbonyloxy, phthalimidyl-2, succinimidyl-2, saccharinyl-2, pyridyl, benzothiazolyl-2-mercapto, ($C_{1-2}$alkoxy)ethoxycarbonyl or benzyloxycarbonyl (preferably by other than benzyloxy); $C_{2-10}$alkyl disubstituted by chloro, bromo, -OH, formyloxy, ($C_{1-4}$alkyl)carbonyloxy, chloro- or bromo-($C_{1-3}$alkyl)carbonyloxy, ($C_{1-4}$alkoxy)carbonyloxy, ($C_{1-2}$alkoxy)ethoxycarbonyloxy, chloro- or bromo-allyloxycarbonyl, $C_{3-4}$alkynyloxy or ($C_{1-2}$alkoxy)ethoxycarbonyl; $C_{1-4}$alkoxy$C_{2-4}$alkyl, in which the alkyl moiety of the alkoxy is monosubstituted by chloro, bromo, cyano, $C_{1-4}$alkoxy, $C_{1-4}$alkoxycarbonyl, $C_{1-4}$alkoxycarbonyloxy or $C_{1-4}$alkylcarbonyloxy; or $C_{3-4}$alkenyl unsubstituted or monosubstituted by phenyl, chloro or bromo; or $R_7$ and $R_8$ together with the N-atom to which they are attached form unsubstituted piperidine or unsubstituted morpholine;

or K″ is a group of formula b, c, d, or e

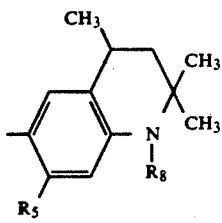

(b)

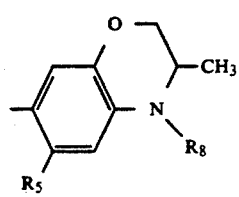

(c)

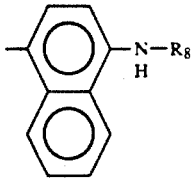

(d)

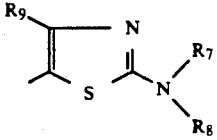

(e)

where $R_9$ is hydrogen, $C_{1-4}$alkyl or phenyl unsubstituted or mono- or di-substituted by methyl, methoxy or chloro, and $R_5$, $R_7$ and $R_8$ are as defined above.

When any significance of $R_7$, $R_8$ or $R_9$ bears two substituents, they may be the same or different.

Preferably $R_5$ is $R_5'$, where $R_5'$ is hydrogen, $C_{1-2}$alkyl or $C_{1-2}$alkylcarbonylamino; more preferably $R_5$ is $R_5''$, where $R_5''$ is hydrogen, methyl or acetylamino.

Preferably $R_6$ is $R_6'$, where $R_6'$ is hydrogen or $C_{1-2}$alkoxy.

Preferably $R_7$ is $R_7'$, where $R_7'$ is $C_{1-6}$alkyl, $C_{1-4}$alkoxy $C_{2-4}$alkyl, $C_{3-4}$alkenyloxy$C_{2-4}$alkyl, $C_{1-2}$alkylcarbonyloxy$C_{2-4}$alkyl, $C_{1-4}$alkoxycarbonyl$C_{2-4}$alkyl, allyl, $C_{1-2}$alkoxycarbonyloxy$C_{2-4}$alkyl or phenoxy $C_{2-4}$alkyl; more preferably $R_7$ is $R_7''$, where $R_7''$ is $C_{2-4}$alkyl, 2-$C_{1-2}$alkoxyethyl or allyl.

Preferably, in $R_7$ and $R_8$ any hydroxy, thiocyano, cyano, acyloxy (e.g., formyloxy, alkylcarbonyloxy and alkoxyethoxycarbonyloxy), alkenyloxy, haloallyloxy, alkynyloxy, alkoxy, phenoxy or substituted alkoxy (e.g. phenylalkoxy and chloroalkoxy) on an alkyl group or moiety attached to a nitrogen or oxygen atom is in other than the 1-position thereof and no two such substituents are attached to a single carbon atom. More preferably, any other non-hydrocarbyl substituent is also in other than the 1-position.

Preferably $R_8$ is $R_8'$, where $R_8'$ is hydrogen, $C_{2-4}$alkyl, $C_{1-4}$alkoxy$C_{2-4}$alkyl, $C_{3-4}$alkenyloxy$C_{2-4}$alkyl, allyl, hydroxy$C_{2-4}$alkyl, $C_{1-2}$alkoxycarbonyloxy$C_{2-4}$alkyl or $C_{1-2}$alkylcarbonyloxy$C_{2-4}$alkyl; more preferably $R_8$ is $R_8''$, where $R_8''$ is hydrogen, $C_{2-4}$alkyl, 2-hydroxy$C_{2-4}$alkyl or allyl.

In $R_7'$ and $R_8'$ any $C_{1-4}$alkoxy, $C_{3-4}$alkenyloxy, ($C_{1-2}$alkyl)carbonyloxy, ($C_{1-2}$alkoxy)carbonyloxy, phenoxy or hydroxy substituent on a $C_{2-4}$alkyl group is in other than the 1-position. Preferably, any other substituent on a $C_{2-4}$alkyl group is also in other than the 1-position.

Preferably, in $R_7$, $R_7'$, $R_8$ and $R_8'$ the double or triple bond of any alkenyl or alkynyl group attached to a nitrogen or oxygen atom is in other than the 1-position.

Preferably K″ is a group of formula a defined above.

More preferably K is K‴, where K‴ is a group of formula a′

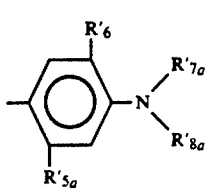

wherein $R_{5a}'$ is hydrogen, $C_{1-2}$alkyl, $C_{1-2}$alkylcarbonylamino unsubstituted or monosubstituted by $C_{1-4}$alkoxy or chloro, or $C_{2-4}$alkenylcarbonylamino;

$R_6'$ is hydrogen or $C_{1-2}$alkoxy;

$R_{7a}'$ is $C_{1-6}$alkyl, $C_{1-4}$alkoxy$C_{2-4}$alkyl, $C_{3-4}$alkenyloxy$C_{2-4}$alkyl, $C_{1-2}$alkylcarbonyloxy$C_{2-4}$alkyl, $C_{1-4}$alkoxy$C_{2-4}$alkyl, allyl, $C_{1-2}$alkoxycarbonyloxy$C_{2-4}$alkyl, benzyloxy-$C_{2-4}$alkyl or phenoxy$C_{2-4}$alkyl; and $R_{8a}'$ is hydrogen, $C_{2-4}$alkyl, $C_{1-4}$alkoxy$C_{2-4}$alkyl, $C_{3-4}$alkenyloxy$C_{2-4}$alkyl, allyl, hydroxy$C_{2-4}$alkyl, $C_{1-2}$alkoxycarbonyloxy-$C_{2-4}$alkyl, $C_{1-2}$alkylcarbonyloxy$C_{2-4}$alkyl, phenyl $C_{1-3}$alkyl, $\gamma$-$C_{3-4}$alkenyloxy-$\beta$-hydroxypropyl or $\gamma$-phenoxy-$\beta$-hydroxypropyl.

Most preferably K is K'''', where K'''' is 2-methyl-4-(N,N-di-$C_{2-4}$alkylamino)phenyl, 2-methyl-4-(N-ethyl-N-$\gamma$-ethoxycarbonylpropylamino)phenyl, 2-methyl-4-(N-ethyl-N-$\gamma$-phenoxypropylamino)phenyl, 2-acetylamino-4-(N-$\beta$-ethoxycarbonylethylamino)-5-ethoxphenyl, 2-acetylamino-4-(N-ethyl-N-allyl-amino)-5-ethoxyphenyl, 2-methyl-4-(N-ethyl-N-$\beta$-hydroxybutylamino) phenyl, 2-acetylamino-4-(N,N-di-$C_{2-3}$alkylamino)phenyl, 2-acetylamino-4-(N,N-di-$C_{2-4}$alkylamino)-5-$C_{1-2}$-alkoxyphenyl, 2-$C_{1-2}$alkoxyacetylamino-4-(N,N-di-$C_{2-3}$alkylamino)phenyl, 2-acetylamino-4-(N-ethyl-N-ethoxycarbonylethylamino)-5-methoxyphenyl, 2-acetylamino-4-(N-1'-chloroallyl-N-ethoxycarbonylethylamino)-5-methoxyphenyl, 2-acryloylamino-4-(N,N-dipropylamino)phenyl, 2-benzoylamino-4-(N,N-di($\beta$-methoxyethylamino)phenyl, 2-methyl-4-(N,N-di-4'-acetoxy-n-butylamino)phenyl, 2-methyl-4-(N-ethyl-N-4'-acetoxy-n-butylamino)phenyl, 2-methyl-4-(N-ethyl-N-$\beta$-benzyloxyethylamino)phenyl, 2-methyl-4-(N-ethyl-N-$\beta$-hydroxy-$\gamma$-allyloxypropylamino)phenyl; 2-methyl-4-(N-ethyl-N-$\beta$-hydroxy-$\gamma$-phenoxypropylamino)phenyl, 2-methyl-4-(N,N-di-$\gamma$-ethoxycarbonylpropylamino)phenyl, 2-methyl-4-(N-ethyl-N-$\gamma$-cyanopropylamino)phenyl or 2-methyl-4-(N-methyl-N-$\gamma$-phenylpropylamino)phenyl (especially the first eight significanes)

Preferred compounds of formula I are those of formula II or III $$\text{Cl}\underset{R'_2}{\overset{R'_1}{\diagdown\diagup S\diagdown\diagup}}\text{NH}_2 \qquad (II)$$

and $$\text{Cl}\underset{R'_2}{\overset{R'_1}{\diagdown\diagup S\diagdown\diagup}}\text{N}=\text{N}-\text{K}'', \qquad (III)$$

more preferably of formula III.

Preferred compounds of formula III are of formula III'

$$\text{Cl}\underset{R''_2}{\overset{R'''_1}{\diagdown\diagup S\diagdown\diagup}}\text{N}=\text{N}-\underset{R'_5}{\overset{R'_6}{\diagdown\diagup}}\text{N}\underset{R'_8}{\overset{R'_7}{\diagdown}} \qquad (III')$$

The more preferred compounds of formula III are of formula III''

$$\text{Cl}\underset{\text{OHC}}{\overset{\text{CN}}{\diagdown\diagup S\diagdown\diagup}}\text{N}=\text{N}-\text{K}'''' \qquad (III'')$$

where K'''' is defined above.

Compounds of formula I in which $R_3$ is —N=N—K can be prepared by coupling to a diazotised compound of formula I where $R_3$ is —NH$_2$ a compound of formula V $$H-K \qquad (V)$$

where the symbols are as defined above.

Compounds of formula I in which $R_3$ is —NH$_2$ can be prepared by reacting a compound of formula VI $$\text{HO}\underset{S}{\overset{R_1}{\diagdown\diagup\diagdown\diagup}}R_{10} \qquad (VI)$$

in which $R_1$ is defined above and $R_{10}$ is a primary amino group, —NHCHO or —NHCOC$_{1-4}$alkyl, with a Vilsmeier reagent to form a compound of formula VII $$R\underset{\text{OHC}}{\overset{R_1}{\diagdown\diagup S\diagdown\diagup}}R_{10} \qquad (VII)$$

followed by hydrolysis of $R_{10}$ to form —NH$_2$ and optional conversion of the formyl group to any of the other significances of $R_2$.

Preferably the Vilsmeier reagent is the reaction product of phosphorus oxychloride and dimethylformamide in which case the compound of formula VII formed is of the formula $$R\underset{\text{OHC}}{\overset{R_1}{\diagdown\diagup S\diagdown\diagup}}\text{N}=\text{CH}-\text{N}(\text{CH}_3)_2$$

which is then hydrolysed in acid or basic medium to a compound of formula I in which $R_2$ is formyl and $R_3$ is —NH$_2$.

Compounds of formulae V and VI are known or may be made by known methods from known compounds. Vilsmeier reagents are also known.

Conversion of the formyl group to another significance of $R_2$ in formula I can be carried out conventionally, for example by condensation with hydroxylamine and optional acylation on the oxygen alone whilst forming the nitrile group or reaction according to the Knoevenagel or Perkin reaction.

It is particularly preferred that the compounds of formula I contain no water-solubilizing groups.

The compounds of formula I in which $R_3$ is —N=N—K will hereinafter be referred to as the dyes of formula I. They are excellent disperse dyes.

The dyes of formula I can be worked up into dyeing preparations in known ways, for example by milling in the presence of dispersing agent or filling material. The preparation so produced (which may be dried in vacuum or by spray-drying) can be used in a long or short dyebath for dyeing, padding or printing material.

The dyes of the invention exhaust onto synthetic or semisynthetic hydrophobic high molecular weight textile material very well from an aqueous suspension. The dyes of the invention are particularly useful for dyeing, padding or printing textile material made from linear aromatic polyester, cellulose 2½ acetate, cellulose triacetate or synthetic polyamide.

Dyeing, printing or padding can be carried out by known methods, in particular according to the methods described in UK Patent 1,114,433.

The resulting dyeings have good fastness properties, in particular good light fastness, good thermofixation, good sublimation fastness and good fastness to pleating.

Many of the azo compounds of formula I, in particular those in which $R_1$ is cyano, have an additional advantage over the known thiophene-2-azo disperse dyes in that they give brilliant neutral to greenish blue-coloured dyeings having attractive hues comparable with the expensive anthraquinone dyes. In these azo compounds, halogen (especially chlorine) as the substituent R produces a surprisingly large bathochromic shift in comparison to the known thiophene-2-azodisperse dyes with hydrogen or alkyl as the substituent R in the same position. The dyeings of azo compounds of formula I in which R is halogen (especially chlorine) are also characterised by a favorable behavior under artificial light, which is a clear advantage compared with a dyeing (same hue under daylight) of the known thiophene-2 azo dyes in which R is methyl or hydrogen; these latter dyeings are characterized by a strong undesired red shift under artificial light.

The invention will now be illustrated by the following Examples in which all parts and percentages are by weight and all temperatures are in °C.

EXAMPLE 1

37.5 Parts of 2-amino-3-ethoxycarbonyl-4-oxo-4,5-dihydrothiophene (described in J. Org. Chem. 38 (20), 3615 [1973]) are dissolved in 152 parts of dimethylformamide, cooled to −10° C. and to this solution 90 parts of phosphorus oxychloride are added whilst stirring well. This mixture is heated to 70° and allowed to cool and is then poured onto 500 parts of ice water. The temperature of the mixture rises to 40° C. The mixture is stirred for ¼ hour, cooled to 5° C. and filtered and the residue is washed with a little ice water. The resulting compound is 2-dimethylamino methylimino-3-ethoxycarbonyl-4-chloro-5-formylthiophene, m.p. 197° C. The product is suspended in 500 parts of water and 25 parts of 85% phosphoric acid are added together with 395 parts of ethyl alcohol and 60 parts of 30% sodium hydroxide. Over two hours and whilst stirring the temperature of the suspension is raised to 65°-70° C. and the pH is maintained at 9 by addition of sodium carbonate. This is then diluted with 300 parts of ice water and the pH is brought to 6.5 by the slow addition of 30% HCl (about 23 parts). 2-Amino-3-ethoxycarbonyl-4-chloro-5-formylthiophene precipitates, m.p. 176°-178°. The product is filtered and washed with a little ice-water. The pure product is recrystallised from ethanol/water, m.p. 180° C.

By reacting the 5-formyl compound with a methylene active compound, derivatives of this product can be produced by known methods.

EXAMPLE 2 a) 122 Parts of 1,1-dicyano-2-methoxypropene together with 32 parts of sulphur powder are suspended in 300 parts of N,N-dimethylformamide, cooled to about 10° and 52 parts of triethylamine are added dropwise over 30 minutes whilst stirring. The temperature of the reaction mixture is allowed to rise to room temperature (25°) and the solution of 2-amino-3-cyano-4-methoxythiophene so formed is poured after stirring for 3 to 4 hours onto 500 g of ice and 150 parts of conc. hydrochloric acid. The mixture that results is stirred 1 to 2 hours and is filtered; the product is 2-amino-3-cyano-4,5-dihydrothiophene-4-one. This is washed with water and then dried.

b) 70 Parts of the product prepared in a) above is dissolved in 400 parts of N,N-dimethylformamide and 230 g of phosphorus oxychloride is added, dropwise over 15 minutes at 5°. Whilst stirring, the reaction temperature is allowed to rise and the mixture is heated to 70° and after 3 to 4 hours is poured onto 1000 parts of ice. Finally, the mixture is neutralised to a pH of about 6 by adding about 450 parts of 25% ammonia and the product 2-(N,N-dimethylformamidino)-3-cyano-4-chloro-5-formylthiophene, m.p. 183° to 188°, is filtered off. The product is recrystallised from acetonitrile, m.p. 191.5° to 193° C.

c) 24.15 Parts of 2-(N,N-dimethylformamidino)-3-cyano-4-chloro-5-formylthiophene are suspended in 100 parts of 50% formic acid. 1 Part of ammonium sulphate is added and the mixture is boiled under reflux for about 5 hours. The mixture is allowed to cool and the product, 2-amino-3-cyano-4-chloro-5-formylthiophene, is filtered off. The amine, without further purifying, is diazotised (as described in Example 16) and coupled. The pure product is recrystallised from a mixture of ethanol and water, m.p. 267° to 269°.

By condensation of the 5-formyl group by known methods (i.e. Knoevenagel reaction, oxime formation and dehydration) derivatives of this compound can be made. Formation of derivatives can be done when the azo compound has already been formed (as described in Example 17).

EXAMPLES 3 to 15

Compounds of the formula

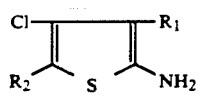

in which $R_1$ and $R_2$ are defined in Table 1 below, can be formed analogously to the method of Example 1 or 2 from suitable reactants.

TABLE 1

| EX. No. | $R_2$ | $R_1$ |
|---|---|---|
| 3 | —CHO | —COOCH$_3$ |
| 4 | " | —COOC$_4$H$_9$ |
| 5 | " | —COOCH$_2$CH$_2$OCH$_3$ |
| 6 | " | —COOCH$_2$C$_6$H$_5$ |
| 7 | " | —SO$_2$C$_6$H$_5$ |
| 8 | —CH=C(CN)(COOC$_4$H$_9$) | —CN |
| 9 | —CH=C(CN)(COOC$_2$H$_5$) | " |

TABLE 1-continued

| EX. No. | R₂ | R₁ |
|---|---|---|
| 10 | —CHO | —CONH-n-C₄H₉ |
| 11 | —CN | —CN |
| 12 | " | —COOC₂H₅ |
| 13 | —CH=C(H)(NO₂) | —CN |
| 14 | —CH=C(CN)(COOCH₂CH₂OCH₃) | " |
| 15 | —CH=C(CN)(COOCH₂C(CH₃)=CH₂) | " |

EXAMPLE 16

23.5 Parts of 2-amino-3-ethoxycarbonyl-4-chloro-5-formylthiophene are dissolved in a mixture of 400 parts acetic acid, 100 parts of propionic acid and 85 parts of phosphoric acid at 30°, then cooled to −5° and at this temperature reacted with 7.0 parts of sodium nitrite (in the form of a 4N solution) at this temperature. A brown solution results. This is stirred for about 2 hours. To this diazonium salt solution a mixture of 18 parts of N,N-diethylamino-m-toluidine, 6 parts of aminosulphonic acid, 10 parts of glacial acetic acid and 50 parts of water is very slowly added whilst stirring and the pH of the mixture is kept at 3.5 to 4 by the addition of 30% NaOH solution. The resulting blue-grey dyestuff suspension is then stirred for a further 2 hours, filtered and the residue is washed with 100 parts of 10% acetic acid followed by 100 parts of water and dried under vacuum at 50° C. The resulting dyestuff is a compound of formula 16a

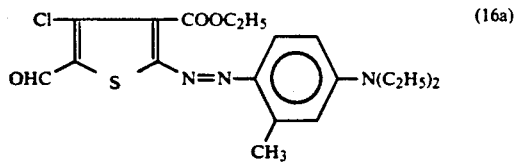

(16a)

and dyes polyester material a blue-violet tone.

EXAMPLE 17

21.3 Parts of the product of formula 16a are dissolved in 150 parts of dioxane at room temperature and are then reacted with 28 parts of cyanoacetic acid methoxyethyl ester followed by a mixture of 2 parts piperidine and 2 parts of glacial acetic acid. After stirring for 20 hours at 25°–30°, no starting material can be detected by thin layer chromatography.

After addition of water, the product precipitates and is filtered, washed with 100 parts of water and vacuum dried at 50°. Using a silica gel column chromatograph, a purified compound of formula 17a

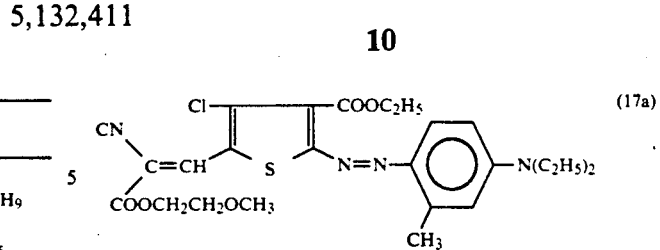

(17a)

results, m.p. 135°–136°.

EXAMPLE 18 a) 18.6 Parts of 2-amino-3-cyano-4-chloro-5-formylthiophene are dissolved in 200 parts of 85% phosphoric acid. Whilst stirring, 33 parts of 40% nitrosylsulphuric acid are added dropwise and the mixture is stirred for 3 hours at about 0°.

The resulting brown diazonium salt solution is added part by part whilst stirring well to a solution of 20.6 parts of 3-(N,N-diethylamino)-1-acetanilide and 2 parts of aminosulphonic acid in 30 parts of 5% sulphuric acid. The coupling temperature of 0°–3° is achieved by external cooling and the addition of about 200 parts of ice. The resulting dyestuff is stirred for 1–2 hours, filtered, washed with about 300 parts of water and dried under vacuum. The resulting product is a compound of formula 18a

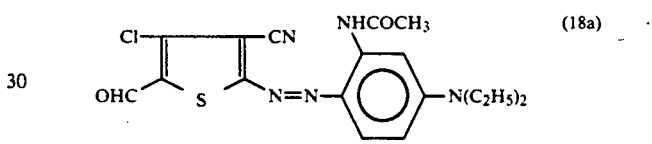

(18a)

which dyes polyester blue tones and has good fastness properties.

b) Instead of using 3-(N,N-diethylamino)-1-acetanilide as the coupling component in the method of Example 18a) above, a mixture of 3-(N,N-di-C₂₋₄alkylamino)-1-acetanilide (prepared by mixed alkylation of 3-amino-1-acetanilide) is used. A dyestuff mixture of formula 18b)

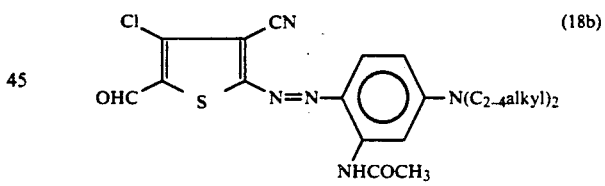

(18b)

results. In Mixture b)1) the alkyl groups are ethyl and n-propyl and in Mixture b)2) they are ethyl and n-butyl, the molar ratio of the two alkyl groups in each mixture being 1:1.

EXAMPLES 19 to 137

Compounds of the formula

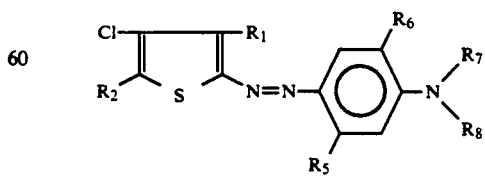

in which the symbols are defined in Table 2 below, can be prepared by a method analogous to Examples 16, 17 and 18 from suitable reactants.

TABLE 2

| EX. No. | R₁ | R₂ | R₅ | R₆ | R₇ | R₈ | Shade on polyester fibre material |
|---|---|---|---|---|---|---|---|
| 19 | —COOC₂H₅ | CHO | —NHCOC₂H₅ | H | —C₂H₅ | —C₂H₅ | violet |
| 20 | " | " | —CH₃ | H | " | " | " |
| 21 | " | " | —NHCOOCH₂CH₂OC₂H₅ | H | " | " | " |
| 22 | " | " | —NHCOCH₃ | H | " | " | " |
| 23 | " | " | " | H | —C₃H₇ | —CH₂CH₂CH₃ | reddish-blue |
| 24 | " | " | —CH₃ | —OCH₃ | " | —CH₂CH₂OH | " |
| 25 | " | " | —NHCOCH₂CH₂OCH₃ | H | —C₂H₅ | —C₂H₅ | navy-blue |
| 26 | " | " | —NHCOCH₃ | —OCH₃ | " | —CH₂CH₂OCOCH₃ | " |
| 27 | " | " | " | —OC₂H₅ | " | " | " |
| 28 | " | " | " | —OCH₂CH₂OCH₃ | " | —CH₂CH₂COOCH₂CH₂OCH₃ | " |
| 29 | " | " | —NHCOC₂H₅ | —OCH₃ | " | " | blue |
| 30 | " | " | —NHCOOCH₂CH₂OC₂H₅ | H | " | —C₂H₅ | " |
| 31 | " | " | H | H | —C₂H₅ | " | reddish-blue |
| 32 | " | " | —CH₃ | H | " | —CH₂CH₂OC₆H₅ | " |
| 33 | " | " | " | H | " | —C₂H₅ | blue |
| 34 | " | —CH=CHNO₂ | " | H | " | —CH₂CH₂OH | blue |
| 35 | —COOC₂H₅ | NC\C=CH—\COOCH₂CH₂CH₂CH₃ | —CH₃ | H | n-C₄H₉ | —CH₂CH₂OH | blue |
| 36 | " | NC\C=CH—\COOCH₂CH₂OCH₃ | —NHCOC₂H₅ | H | —C₂H₅ | —C₂H₅ | greenish-blue |
| 37 | " | NC\C=CH—\COOCH₂CH₂OCH₃CH₃ | H | H | " | " | blue |
| 38 | " | " | —CH₃ | H | " | " | greenish-blue |
| 39 | " | —CHO | —NHCOC₂H₅ | H | " | " | " |
| 40 | —COOCH₃ | " | —CH₃ | H | " | " | bluish-violet |
| 41 | " | " | —NHCOC₂H₅ | H | " | " | blue |
| 42 | " | O₂NHC=CH— | " | H | " | " | greenish-blue |
| 43 | —COOCH₂CH₂OCH₃ | NC\C=CH—\COOCH₂CH₂CH₃ | " | H | " | " | " |
| 44 | —CN | —CHO | —CH₃ | H | —C₂H₅ | —C₂H₅ | blue |
| 45 | " | " | " | H | n-C₃H₇ | n-C₃H₇ | " |
| 46 | " | " | " | H | —C₂H₅ | n-C₄H₉ | " |

TABLE 2-continued

| Ex. No. | $R_1$ | $R_2$ | $R_5$ | $R_6$ | $R_7$ | $R_8$ | Shade on polyester fibre material |
|---|---|---|---|---|---|---|---|
| 47 | " | " | H | H | " | n-$C_6H_{13}$ | " |
| 48 | " | " | —NHCO$C_2H_4$O$C_2H_5$ | H | " | —$C_2H_5$ | " |
| 49 | " | " | —NHCOCH$_3$ | H | " | —$C_3H_7$ | " |
| 50 | " | " | —NHCO$C_2H_5$ | H | —$C_3H_7$ | n-$C_3H_7$ | " |
| 51 | " | " | " | H | " | " | " |
| 52 | " | —CHO | —NHCOCH$_2$CH$_2$Cl | H | —$C_2H_5$ | —$C_2H_5$ | " |
| 53 | " | " | —NHCO$C_2H_4$OCH$_3$ | H | " | " | " |
| 54 | " | " | —NHCO$C_2H_4$COO$C_2H_5$ | H | " | " | " |
| 55 | " | " | —NHCO$CH_2$COOCH$_3$ | H | " | " | " |
| 56 | " | " | —NHCOCH=CH$_2$ | H | " | " | " |
| 57 | " | " | —NHCOCH$_3$ | H | " | " | greenish-blue |
| 58 | " | " | " | —OCH$_3$ | —CH$_2$—CH=CH$_2$ | —CH$_2$—CH=CH$_2$ | " |
| 59 | " | " | —CH$_3$ | —OC$_2H_5$ | —$C_2H_5$ | —$C_2H_5$ | " |
| 60 | " | " | —CH$_3$ | H | —CH$_2$CH$_2$OCOCH$_3$ | —CH$_2$CH$_2$OCOCH$_3$ | " |
| 61 | " | " | " | H | —$C_2H_5$ | —$C_2H_5$ | " |
| 62 | " | " | " | H | n-$C_3H_7$ | —$C_3H_7$ | " |
| 63 | —CN | —CN | " | H | n-$C_4H_9$ | n-$C_4H_9$ | " |
| 64 | " | —CN | " | H | —$C_2H_5$ | —$C_2H_5$ | " |
| 65 | " | " | —NHCOCH$_3$ | H | " | —$C_3H_6O$—$C_6H_5$ | " |
| 66 | " | —CHO | —NHCOCH$_3$ | —OCH$_3$ | —$C_2H_4$COO(CH$_2$)$_3$CH$_3$ | H | blue |
| 67 | " | " | " | —OC$_2H_5$ | —$C_2H_4$COOCH$_3$ | H | blue |
| 68 | " | —CN | " | H | —$C_2H_5$ | —$C_2H_5$ | greenish-blue |
| 69 | " | " | " | H | n-$C_3H_7$ | —$C_3H_7$ | blue |
| 70 | " | " | " | —OC$_2H_5$ | —$C_3H_4$COOCH$_3$ | H | " |
| 71 | " | " | " | —OCH$_3$ | —CH(CH$_3$)$C_2H_5$ | n-$C_4H_9$ | " |
| 72 | —CN | —CHO | —NHCOCH$_3$ | H | —$C_2H_5$ | —$C_2H_5$ | " |
| 73 | " | " | —NHCO$C_2H_5$ | H | —CH$_2$—CH=CH$_2$ | —CH$_2$—CH=CH$_2$ | greenish-blue |
| 74 | " | " | —NHCOCH$_3$ | H | —$C_2H_5$ | —CH$_2$CH$_2$OCOCH$_3$ | " |
| 75 | " | " | " | H | —CH$_2$CH$_2$OCOCH$_3$ | —CH$_2$CH=CHCl | " |
| 76 | " | " | " | —OC$_2H_5$ | —$C_2H_5$ | —CH$_2$—CH=CH$_2$ | greenish-blue |
| 77 | " | " | —OCH$_3$ | H | —CH$_2$CH$_2$OCOCH$_3$ | H | " |
| 78 | " | $Z_1^*$ | —OC$_2H_5$ | H | —CH$_2$CH$_2$COOCH$_3$ | H | " |
| 79 | " | $Z_2^{**}$ | —NHCOCH$_3$ | H | —CH$_2$CH$_2$COOCH$_3$—CH=CHCl | H | " |
| 80 | " | " | " | " | —CH$_2$CH$_2$OCH$_3$ | " | " |
| 81 | " | " | " | " | " | —CH$_2$CH$_2$OCH$_3$ | " |
| 82 | " | " | " | " | " | —CH$_2$CH=CH$_2$ | " |
| 83 | —CN | —CHO | " | —OC$_2H_5$ | —CH$_2$CH$_2$CN | —CH$_2$CH$_2$OCH$_3$ | greenish-blue |
| 84 | " | —CN | —CH$_3$ | H | —CH$_2$CH$_2$COOCH$_3$ | —CH$_2$CH=CH$_2$ | " |
| 85 | " | —CHO | " | H | —$C_2H_5$ | —$C_2H_5$ | " |
| 86 | " | $Z_1^*$ | " | H | " | —$C_2H_5$ | " |
| 87 | " | $Z_2^{**}$ | " | H | " | " | " |
| 88 | " | —CHO | —NHCOCH$_3$ | H | —$C_2H_4$CN | —$C_2H_5$ | greenish-blue |
| 89 | " | " | —NHCOCH$_3$ | —OCH$_3$ | —$C_2H_4$OCH$_2$CH=CH$_2$ | —$C_2H_4$OCH$_2$CH=CH$_2$ | " |
| 90 | —CN | " | " | " | n-$C_4H_9$ | n-$C_4H_9$ | " |

TABLE 2-continued

| EX. No. | R$_1$ | R$_2$ | R$_5$ | R$_6$ | R$_7$ | R$_8$ | Shade on polyester fibre material |
|---|---|---|---|---|---|---|---|
| 97 | " | " | " | " | —n-C$_3$H$_7$ | —C$_2$H$_5$ | " |
| 98 | " | " | " | " | " | —n-C$_3$H$_7$ | " |
| 99 | " | " | —NHCOC$_2$H$_4$OCH$_3$ | —OC$_2$H$_5$ | —C$_2$H$_4$OCH$_3$ | —C$_2$H$_4$OCH$_3$ | " |
| 100 | " | " | —NHCOCH$_3$ | —OC$_2$H$_4$OCH$_3$ | —C$_2$H$_4$COOCH$_3$ | H | " |
| 101 | " | " | —NHCOOCH$_3$ | —OC$_2$H$_5$ | —C$_2$H$_5$ | —CH$_3$ | " |
| 102 | " | " | —NHCOOC$_2$H$_4$OC$_2$H$_5$ | " | —C$_2$H$_4$OCH$_3$ | —C$_2$H$_4$OCOCH$_3$ | " |
| 103 | " | " | —NHCOCH$_3$ | " | —C$_2$H$_5$ | —C$_2$H$_5$ | " |
| 104 | " | " | —NHCOCH$_3$ | " | —C$_2$H$_5$ | —C$_2$H$_5$ | " |
| 105 | " | " | " | " | —C$_2$H$_4$COOC$_2$H$_5$ | H | " |
| 106 | " | " | " | " | —C$_2$H$_4$COOCH$_2$CH=CH$_2$ | H | " |
| 107 | " | " | " | " | —C$_2$H$_4$COOCH$_2$—C(CH$_3$)=CH$_2$ | H | " |
| 108 | " | " | " | " | —C$_2$H$_4$COOCH$_2$COOCH$_3$ | H | " |
| 109 | " | " | —NHCOCH$_3$ | —OCH$_3$ | " | H | greenish-blue |
| 110 | —CN | —CN | " | —OCH$_3$ | —C$_2$H$_5$ | —n-C$_4$H$_9$ | " |
| 111 | " | —CHO | " | " | —C$_2$H$_4$OCH$_3$ | —C$_2$H$_5$ | blue |
| 112 | " | —CN | " | " | " | —C$_2$H$_4$OCH$_3$ | " |
| 113 | " | —CHO | " | " | " | —C$_2$H$_5$ | " |
| 114 | " | " | " | H | —(CH$_2$)$_3$—O—C$_6$H$_5$ | " | " |
| 115 | " | " | " | H | —(CH$_2$)$_3$COOC$_2$H$_5$ | —(CH$_2$)$_4$OCOCH$_3$ | " |
| 116 | " | " | " | H | —(CH$_2$)$_4$OCOCH$_3$ | " | " |
| 117 | " | " | H | H | —C$_2$H$_4$OC$_6$H$_5$ | " | " |
| 118 | " | " | —CH$_3$ | H | —C$_2$H$_4$OC$_6$H$_5$ | " | " |
| 119 | " | " | " | H | —C$_2$H$_4$OCH$_2$—C$_6$H$_5$ | —C$_2$H$_5$ | " |
| 120 | " | " | " | H | —(CH$_2$)$_3$COOC$_2$H$_5$ | " | " |
| 121 | " | " | " | H | —(CH$_2$)$_3$OC$_6$H$_4$—4-CH$_3$ | " | " |
| 122 | " | " | " | H | —CH$_2$CHOHCH$_2$Cl | " | " |
| 123 | " | " | " | H | —CH$_2$CHOHCH$_2$C$_6$H$_5$ | " | " |
| 124 | " | " | " | H | —CH$_2$CHOHCH$_2$OCOCH$_3$ | " | " |
| 125 | —CN | —CHO | —OCH$_3$ | —OCH$_3$ | —C$_2$H$_4$OCOCH$_3$ | —C$_2$H$_4$OCOCH$_3$ | " |
| 126 | " | " | " | " | —CH$_2$CHOHCH$_2$OC$_6$H$_5$ | —CH$_3$ | " |
| 127 | " | " | " | " | —CH$_2$CHOHCH$_2$CH=CHCl | H | " |
| 128 | " | " | " | " | —C$_2$H$_4$COOCH$_2$CH=CHCl | H | " |
| 129 | " | " | —CH$_3$ | H | —C$_2$H$_4$OCH$_2$C$_6$H$_5$ | H | " |
| 130 | " | " | —CH$_3$ | H | —(CH$_2$)$_3$OC$_6$H$_5$ | H | " |
| 131 | " | " | " | H | —CH$_2$—CH=CH$_2$ | —CH$_2$—CH=CH$_2$ | " |
| 132 | " | " | " | H | —CH$_2$—CH=CH$_2$ | —C$_2$H$_5$ | blue |
| 133 | " | " | " | H | —CH$_2$CH$_2$O(CH$_2$)$_2$CN | " | " |
| 134 | " | " | —OCH$_3$ | H | —CH$_2$CH$_2$OCH$_2$CH=CH$_2$ | —CH$_3$ | " |
| 135 | " | " | " | H | —CH$_2$CHOHCH$_2$OC$_6$H$_5$ | " | " |
| 136 | " | " | " | H | —C$_2$H$_4$COOCH$_2$OCOCH$_3$ | —CH$_2$CH$_2$OCOCH$_3$ | " |
| 137 | " | " | " | H | —CH$_2$CH$_2$CH$_2$OCOCH$_3$ | " | " |
| 138 | " | " | " | H | —CH$_2$CH$_2$CH$_2$CN | " | " |
| 139 | " | " | —CH$_3$ | H | —CH$_2$CH$_2$C$_6$H$_5$ | " | redish blue |
| 140 | —CN | —CHO | —NHCOCH$_3$ | —OCH$_3$ | —CH$_2$CH$_2$COOC$_2$H$_5$ | —CH$_2$CH$_2$CH$_2$OCOCH$_3$ | " |
| 141 | " | " | " | H | —CH$_2$CH$_2$COOC$_2$H$_5$ | —C$_2$H$_5$ | redish blue |
| 142 | " | " | " | H | —C$_2$H$_5$ | —C$_2$H$_5$ | greenish blue |
| 143 | " | " | —NHCOC$_6$H$_5$ | H | —CH$_2$CH$_2$OCH$_3$ | —CH$_3$ | " |
| 144 | " | " | —NHCOCH=CH$_2$ | H | " | —CH$_2$CH=CHCl | " |
| 145 | " | " | —NHCOCH$_2$OC$_2$H$_5$ | H | —n-C$_3$H$_7$ | —CH$_2$CH$_2$OCH$_3$ | " |
| 146 | " | " | —NHCOCH$_2$OCH$_3$ | H | —C$_2$H$_5$ | —C$_2$H$_5$ | " |

TABLE 2-continued

| EX. No. | $R_1$ | $R_2$ | $R_5$ | $R_6$ | $R_7$ | $R_8$ | Shade on polyester fibre material |
|---|---|---|---|---|---|---|---|
| 147 | " | " | —NHCOCH$_3$ | —OCH$_3$ | " | —CH$_2$—CH=CHCl | " |
| 148 | " | " | " | —OC$_2$H$_5$ | " | —CH$_2$—CH=CH$_2$ | " |

$$Z_1^* = -CH = C\begin{matrix} CN \\ COOC_2H_5 \end{matrix}$$

$$Z_2^{**} = -CH = C\begin{matrix} CN \\ COOC_4H_9 \end{matrix}$$

EXAMPLES 149 to 158

Compounds of the formula

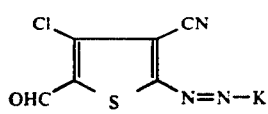

in which K is defined in Table 3 below can be prepared by a method analogous to that of Example 18 from suitable reactants.

TABLE 3

| Ex. No. | K | Shade |
|---|---|---|
| 149 | ![structure] (methylphenyl with N(CH₃)(C₂H₅) and C(CH₃)₂ group) | greenish-blue |
| 150 | ![structure] (trimethylphenyl with N(CH₃)(C₂H₄OH)) | greenish-blue |
| 151 | ![structure] (methyl-NHCOCH₃-phenyl with N(CH₃)(C₂H₅)) | greenish-blue |
| 152 | ![structure] (methylphenyl with OCH(CH₃)... N(CH₂)₃CH₃) | greenish-blue |
| 153 | naphthyl—NH—CH₂CHOHCH₂OH | greenish-blue |
| 154 | naphthyl—NHCH₂CHOHCH₂OCH₂C≡CH | greenish-blue |
| 155 | naphthyl—NHC₂H₄COOC₂H₅ | greenish-blue |
| 156 | $H_5C_6$–C=C(CH₃)–S–C(=N–)–N(CH₂CH₂CH₂CH₃)₂ (thiazole) | blue |
| 157 | $H_5C_6$–C=C(CH₃)–S–C(=N–)–NHC₆H₅ (thiazole) | blue |
| 158 | $H_5C_6$–C=C(CH₃)–S–C(=N–)–morpholine (thiazole) | blue |

APPLICATION EXAMPLE

(a) Production of a dyeing preparation 10 g of the dyestuff of Example 18a, 9.3 g of sodium lignin sulphonate and 25 ml of demineralised water are stirred in a 150 ml beaker with a two plate stirrer at 150-200 revs. per minute. If a homogeneous paste results the rate of stirring is increased to a maximum of 1500-2000 revs. per minute whilst 156 g (=85 ml) of siliquarzite pearls (31-5/31-7 1:1) are added until a viscous grindable surface layer results. The material is slowly ground whilst cooling in a continuous flowing water bath until a fluid sample no longer produces a ring on filter paper. The stirring is then reduced 500 revs. per minute and the mass is reacted with a solution of 9.3 g of sodium lignin sulphonate and 20 ml of demineralized water as a result of which the mass becomes slightly fluid. The mass is mixed well for 10 minutes, filtered through a glass filter flask G2 and rinsed with 300 ml of demineralised water.

The dispersion has a pH of 9.0-9.5 and is brought to pH of 6.5 by the addition of a 10% phosphoric acid solution.

Finally the dispersion is dried and then finely pulverized in a mill.

Instead of a dyestuff of Example 18a any one of the dyestuffs of Examples 16 to 155 may be used in an appropriate amount.

(b) Dyeing

5 Parts of a precleaned polyester web are immersed in a high temperature dyeing bath in 100 parts of a dyebath heated to 70°, the 100 parts of dyebath comprising 0.05 of the above-mentioned dyeing preparation of the dyestuff of Example 18a and 2 parts ammonium sulphate, the balance being water and the bath is brought to pH 5 by the addition of formic acid. The dyeing apparatus is then closed and heated over 20 minutes to 130° and then maintained at this temperature for a further 60 minutes. After cooling the polyester web is removed from the dyebath, rinsed, soaped, rinsed again and dried. A level deep blue dyeing results with good fastness properties. The remaining dyebath is practically colourless.

Instead of the dyeing preparations of the dyestuff of Example 18a the dyeing preparations of a dyestuff of any one of Examples 16 to 155 may be used.

What is claimed is:

1. A compound of the formula

wherein
K is a coupling component radical,
R is halo,
$R_1$ is cyano; $(C_{1-6}alkoxy)carbonyl$; $(C_{3-6}alkenyl)oxycarbonyl$; $C_{1-4}alkylsulfonyl$; phenylsulfonyl; $(C_{1-4}alkyl)carbonyl$; benzoyl; carbamoyl; $(C_{1-4}alkyl)carbamoyl$; N,N-di-$(C_{1-4}alkyl)carbamoyl$; phenylcarbamoyl; benzyloxycarbonyl; or $(C_{1-6}alkoxy)carbonyl$, $(C_{3-6}alkenyl)oxycarbonyl$, $C_{1-4}alkylsulfonyl$, phenylsulfonyl or $(C_{1-4}alkyl)carbamoyl$ substituted by one or two substituents independently selected from chloro, bromo, $C_{1-4}alkyl$, $C_{1-4}alkoxy$, hydroxy, cyano and acyl, and
$R_2$ is formyl, cyano, —CH=C($R_4$)$_2$ or —CH=N—OH,
wherein (1) each $R_4$ is independently cyano; $(C_{1-6}alkoxy)carbonyl$; $(C_{3-6}alkenyl)oxycarbonyl$; $(C_{3-6}alkynyl)oxycarbonyl$; or $(C_{1-6}alkoxy)carbonyl$, $(C_{3-6}alkenyl)oxycarbonyl$ or $(C_{3-6}alkynyl)oxycarbonyl$ substituted by one or two substituents independently selected from chloro, bromo, $C_{1-4}alkyl$, $C_{1-4}alkoxy$, hydroxy, cyano and acyl,
(2) one $R_4$ is cyano and the other is benzoyl or benzoyl monosubstituted by $(C_{1-4}alkoxy)carbonyl$, $C_{1-4}alkylsulfonyl$, phenylsulfonyl, carbamoyl, $(C_{1-4}alkyl)carbamoyl$, phenylcarbamoyl or $(C_{1-4}alkoxy)carbonyl$, $C_{1-4}alkylsulfonyl$, phenylsulfonyl or $(C_{1-4}alkyl)carbamoyl$ substituted by one or two substituents independently selected from chloro, bromo, $C_{1-4}alkyl$, $C_{1-4}alkoxy$, hydroxy, cyano and acyl,
(3) one $R_4$ is hydrogen and the other is benzoyl; benzoyl monosubstituted by $(C_{1-2}alkoxy)carbonyl$, halo, $C_{1-4}alkyl$, nitro or $(C_{1-2}alkoxy)carbonyl$ substituted by one or two substituents independently selected from chloro, bromo, $C_{1-4}alkyl$, $C_{1-4}alkoxy$, hydroxy, cyano and acyl; $(C_{1-4}alkyl)carbonyl$ or $(C_{3-6}alkenyl)carbonyl$ or
(4) one $R_4$ is nitro and other is hydrogen, methyl or ethyl,
wherein each halo is independently chloro or bromo.

2. A compound according to claim 1 wherein
$R_1$ is cyano; $(C_{1-6}alkoxy)carbonyl$; $(C_{3-6}alkenyl)oxycarbonyl$; $C_{1-4}alkylsulfonyl$; phenylsulfonyl; $(C_{1-4}alkyl)carbonyl$; benzoyl; carbamoyl; $(C_{1-4}alkyl)carbamoyl$; N,N-di-$(C_{1-4}alkyl)carbamoyl$; phenylcarbamoyl; benzyloxycarbonyl; or $(C_{1-6}alkoxy)carbonyl$, $(C_{3-6}alkenyl)oxycarbonyl$, $C_{1-4}alkylsulfonyl$, phenylsulfonyl or $(C_{1-4}alkyl)carbamoyl$ monosubstituted by chloro, bromo, $C_{1-4}alkyl$, $C_{1-4}alkoxy$, hydroxy, cyano, $(C_{1-4}alkyl)carbonyl$ or $(C_{1-4}alkoxy)carbonyl$, and
$R_2$ is formyl, cyano, —CH=C($R_4$)$_2$ or —CH=N—OH,
wherein (1) each $R_4$ is independently cyano; $(C_{1-6}alkoxy)carbonyl$; $(C_{3-6}alkenyl)oxycarbonyl$; $(C_{3-6}alkynyl)oxycarbonyl$; or $(C_{1-6}alkoxy)carbonyl$, $(C_{3-6}alkenyl)oxycarbonyl$ or $(C_{3-6}alkynyl)oxycarbonyl$ monosubstituted by chloro, bromo, $C_{1-4}alkyl$, $C_{1-4}alkoxy$, hydroxy, cyano, $(C_{1-4}alkyl)carbonyl$ or $(C_{1-4}alkoxy)carbonyl$,
(2) one $R_4$ is cyano and the other is benzoyl or benzoyl monosubstituted by $(C_{1-4}alkoxy)carbonyl$, $C_{1-4}alkylsulfonyl$, phenylsulfonyl, carbamoyl, $(C_{1-4}alkyl)carbamoyl$, phenylcarbamoyl or $(C_{1-4}alkoxy)carbonyl$, $C_{1-4}alkylsulfonyl$, phenylsulfonyl or $(C_{1-4}alkyl)carbamoyl$ monosubstituted by chloro, bromo, $C_{1-4}alkyl$, $C_{1-4}alkoxy$, hydroxy, cyano, $(C_{1-4}alkyl)carbonyl$ or $(C_{1-4}alkoxy)carbonyl$,
(3) one $R_4$ is hydrogen and the other is benzoyl; benzoyl monosubstituted by $(C_{1-2}alkoxy)carbonyl$, halo, $C_{1-4}alkyl$, nitro or $(C_{1-2}alkoxy)carbonyl$ monosubstituted by chloro, bromo, $C_{1-4}alkyl$, $C_{1-4}alkoxy$, hydroxy, cyano, $(C_{1-4}alkyl)carbonyl$ or $(C_{1-4}alkoxy)carbonyl$; $(C_{1-4}alkyl)carbonyl$ or $(C_{3-6}alkenyl)carbonyl$ or
(4) one $R_4$ is nitro and the other is hydrogen, methyl or ethyl.

3. A compound according to claim 2 wherein
$R_1$ is cyano, $(C_{1-6}alkoxy)carbonyl$, $(C_{3-6}alkenyl)oxycarbonyl$, $C_{1-4}alkylsulfonyl$, phenylsulfonyl, $(C_{1-4}alkyl)carbonyl$, benzoyl, carbamoyl, $(C_{1-4}alkyl)carbamoyl$, N,N-di-$(C_{1-4}alkyl)carbamoyl$, phenylcarbamoyl or benzyloxycarbonyl, and
$R_2$ is formyl, cyano, —CH=C($R_4$)$_2$ or —CH=N—OH,
wherein (1) each $R_4$ is independently cyano, $(C_{1-6}alkoxy)carbonyl$, $(C_{3-6}alkenyl)oxycarbonyl$ or $(C_{3-6}alkynyl)oxycarbonyl$,
(2) one $R_4$ is cyano and the other is benzoyl or benzoyl monosubstituted by $(C_{1-4}alkoxy)carbonyl$, $C_{1-4}alkylsulfonyl$, phenylsulfonyl, carbamoyl, $(C_{1-4}alkyl)carbamoyl$ or phenylcarbamoyl,
(3) one $R_4$ is hydrogen and the other is benzoyl; benzoyl monosubstituted by $(C_{1-2}alkoxy)carbonyl$, halo, $C_{1-4}alkyl$ or nitro; $(C_{1-4}alkyl)carbonyl$ or $(C_{3-6}alkenyl)carbonyl$ or
(4) one $R_4$ is nitro and the other is hydrogen, methyl or ethyl.

4. A compound according to claim 2 having the formula

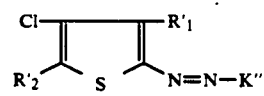

wherein K″ is

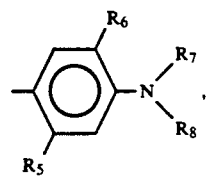

-continued

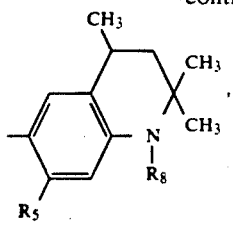

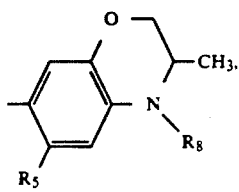

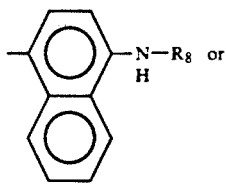

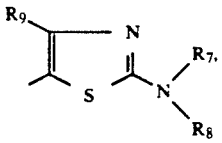

wherein

R$_5$ is hydrogen; C$_{1-2}$alkyl; C$_{1-2}$alkoxy; formamido; (C$_{1-4}$alkyl)carbonylamino; (C$_{1-4}$alkyl)carbonylamino the alkyl group of which is monosubstituted by hydroxy, chloro, bromo, C$_{1-4}$alkoxy, phenyl, phenoxy, benzyloxy or (C$_{1-2}$alkoxy)carbonyl; benzamido; acryloylamino; aminocarbonylamino; (C$_{1-4}$alkyl)aminocarbonylamino; (C$_{1-4}$alkoxy)carbonylamino; (C$_{1-4}$alkoxy)carbonylamino the alkoxy group of which is monosubstituted by C$_{1-2}$alkoxy or phenyl; C$_{1-2}$alkylsulfonylamino; phenylsulfonylamino; N,N-di-(C$_{1-2}$alkyl)aminosulfonylamino; fluoro; chloro or bromo, R$_6$ is hydrogen, fluoro, chloro, bromo, C$_{1-2}$alkyl, C$_{1-4}$alkoxy or (C$_{1-2}$alkoxy)ethoxy, with the proviso that when R$_5$ is fluoro, chloro or bromo, R$_6$ is other than fluoro, chloro and bromo, R$_7$ is hydrogen; C$_{1-10}$alkyl; C$_{2-10}$alkyl monosubstituted by chloro, bromo, hydroxy, cyclohexyl, thiocyanato, cyano, (C$_{1-4}$alkyl)carbonyl, (C$_{1-4}$alkoxy)carbonyl, formyloxy, (C$_{1-10}$alkyl)carbonyloxy, chloro(C$_{1-3}$alkyl)carbonyloxy, bromo(C$_{1-3}$alkyl)carbonyloxy, (C$_{1-10}$alkoxy)carbonyloxy, (C$_{1-2}$alkoxy)ethoxycarbonyloxy, (C$_{3-4}$alkenyl)oxycarbonyl, chloroallyloxycarbonyl, bromoallyloxycarbonyl, C$_{3-4}$alkenyloxy, chloroallyloxy, bromoallyloxy, C$_{3-4}$alkynyloxy, benzoyloxy, C$_{1-10}$alkoxy, phenyl, phenoxy, phenyl(C$_{1-4}$alkoxy), (C$_{1-2}$alkoxy)ethoxycarbonyl or benzyloxycarbonyl; C$_{2-10}$alkyl substituted by two substituents selected from chloro, bromo, hydroxy, formyloxy, (C$_{1-4}$alkyl)carbonyloxy, chloro(C$_{1-3}$alkyl)carbonyloxy, bromo(C$_{1-3}$alkyl)carbonyloxy, (C$_{1-4}$alkoxy)carbonyloxy, (C$_{1-2}$alkoxy)ethoxycarbonyloxy, chloroallyloxycarbonyl, bromoallyloxycarbonyl, C$_{3-4}$alkynyloxy and (C$_{1-2}$alkoxy)ethoxycarbonyl; (C$_{1-4}$alkoxy)C$_{2-6}$alkyl the alkyl moiety of the alkoxy group of which is monosubstituted by chloro, bromo, cyano, C$_{1-4}$alkoxy, (C$_{1-4}$alkoxy)carbonyl, (C$_{1-4}$alkoxy)carbonyloxy or (C$_{1-4}$alkyl)carbonyloxy; β-[(C$_{1-4}$alkoxy)carbonylmethoxycarbonyl]ethyl; C$_{3-4}$alkenyl; C$_{3-4}$alkenyl monosubstituted by phenyl, chloro or bromo; propynyl; C$_{5-7}$-cycloalkyl; cyclohexyl monosubstituted, disubstituted or trisubstituted by methyl; phenyl; phenyl monosubstituted by chloro, bromo, nitro, C$_{1-4}$alkoxy or methyl or disubstituted or trisubstituted by methyl; or β-hydroxypropyl monosubstituted by γ-C$_{1-4}$alkoxy, γ-C$_{3-4}$alkenyloxy or γ-phenoxy, R$_8$ is hydrogen; C$_{1-10}$alkyl; C$_{2-10}$alkyl monosubstituted by chloro, bromo, hydroxy, cyano, thiocyanato, (C$_{1-10}$alkyl)carbonyl, (C$_{1-10}$alkoxy)carbonyl, formyloxy, (C$_{1-10}$alkyl)carbonyloxy, chloro(C$_{1-4}$alkyl)carbonyloxy, bromo(C$_{1-4}$alkyl)carbonyloxy, (C$_{1-10}$alkoxy)carbonyloxy, (C$_{1-2}$alkoxy)ethoxycarbonyloxy, (C$_{3-4}$alkenyl)oxycarbonyl, chloroallyloxycarbonyl, bromoallyloxycarbonyl, C$_{3-4}$alkenyloxy, chloroallyloxy, bromoallyloxy, C$_{3-4}$alkynyloxy, benzoyloxy, C$_{1-10}$alkoxy, phenyl, phenoxy, phenyl(C$_{1-4}$alkoxy), carbamoyl, (C$_{1-4}$alkyl)carbamoyl, N,N-di-(C$_{1-4}$alkyl)carbamoyl, phenylcarbamoyl, (C$_{1-4}$alkyl)carbamoyloxy, N,N-di-(C$_{1-4}$alkyl)carbamoyloxy, phenylcarbamoyloxy, phthalimidyl-2, succinimidyl-2, saccharinyl-2, pyridyl, benzothiazolyl-2-mercapto, (C$_{1-2}$alkoxy)ethoxycarbonyl or benzyloxycarbonyl; C$_{2-10}$alkyl substituted by two substituents selected from chloro, bromo, hydroxy, formyloxy, (C$_{1-4}$alkyl)carbonyloxy, chloro(C$_{1-3}$alkyl)carbonyloxy, bromo(C$_{1-3}$alkyl)carbonyloxy, (C$_{1-4}$alkoxy)carbonyloxy, (C$_{1-2}$alkoxy)ethoxycarbonyloxy, chloroallyloxycarbonyl, bromoallyloxycarbonyl, C$_{3-4}$alkynyloxy and (C$_{1-2}$alkoxy)ethoxycarbonyl; (C$_{1-4}$alkoxy)C$_{2-4}$alkyl the alkyl moiety of the alkoxy group of which is monosubstituted by chloro, bromo, cyano, C$_{1-4}$alkoxy, (C$_{1-4}$alkoxy)carbonyl, (C$_{1-4}$alkoxy)carbonyloxy or (C$_{1-4}$alkyl)carbonyloxy; C$_{3-4}$alkenyl or C$_{3-4}$alkenyl monosubstituted by phenyl, chloro or bromo, or —NR$_7$R$_8$ is piperidino or morpholino, and R$_9$ is hydrogen, C$_{1-4}$alkyl, phenyl or phenyl substituted by one or two substituents selected from methyl, methoxy and chloro, R$_1'$ is cyano, (C$_{1-4}$alkoxy)carbonyl, (C$_{3-4}$alkenyl)oxycarbonyl, (C$_{1-4}$alkoxy) (C$_{2-4}$alkoxy)carbonyl, benzyloxycarbonyl, (C$_{1-4}$alkyl)carbamoyl, C$_{1-4}$alkylsulfonyl or phenylsulfonyl, and R$_2'$ is formyl, cyano or —CH=C(R$_4'$)$_2$,
wherein each R$_4'$ is independently cyano, (C$_{1-6}$alkoxy)carbonyl, (C$_{3-6}$alkenyl)oxycarbonyl or 2-(C$_{1-4}$alkoxy)ethoxycarbonyl or
one R$_4'$ is nitro and the other is hydrogen.

5. A compound according to claim 4 having the formula

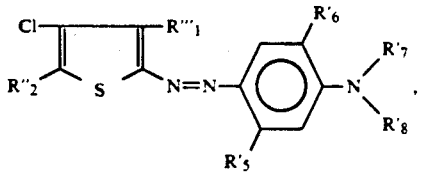

wherein $R_1'''$ is cyano or ($C_{1-2}$alkoxy)carbonyl, $R_2''$ is formyl or cyano, $R_5'$ is hydrogen, $C_{1-2}$alkyl or ($C_{1-2}$alkyl)carbonylamino, $R_6'$ is hydrogen or $C_{1-2}$alkoxy, $R_7'$ is $C_{1-6}$alkyl, ($C_{1-4}$alkoxy)$C_{2-4}$alkyl, ($C_{3-4}$alkenyl)oxy($C_{2-4}$alkyl), ($C_{1-2}$alkyl)carbonyloxy($C_{2-4}$alkyl), ($C_{1-4}$alkoxy)carbonyl($C_{2-4}$alkyl), allyl, ($C_{1-2}$alkoxy)carbonyloxy($C_{2-4}$alkyl) or phenoxy($C_{2-4}$alkyl), and $R_8'$ is hydrogen, $C_{2-4}$alkyl, ($C_{1-4}$alkoxy)$C_{2-4}$alkyl, ($C_{3-4}$alkenyl)oxy($C_{2-4}$alkyl), allyl, hydroxy($C_{2-4}$alkyl), ($C_{1-2}$alkoxy)carbonyloxy($C_{2-4}$alkyl) or ($C_{1-2}$alkyl)carbonyloxy($C_{2-4}$alkyl).

6. A compound according to claim 5 having the formula

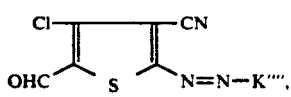

wherein K'''' is 2-methyl-4-[N,N-di-($C_{2-4}$alkyl)amino]phenyl, 2-methyl-4-(N-ethyl-N-γ-ethoxycarbonylpropylamino)phenyl, 2-methyl-4-(N-ethyl-N-γ-phenoxypropylamino)phenyl, 2-acetamido-4-(N-β-ethoxycarbonylethylamino)-5-ethoxyphenyl, 2-acetamido-4-(N-ethyl-N-allylamino)-5-ethoxyphenyl, 2-methyl-4-(N-ethyl-N-β-hydroxybutylamino)phenyl, 2-acetamido-4-[N,N-di-($C_{2-3}$alkyl)amino]phenyl or 2-acetamido-4-[N,N-di-($C_{2-4}$alkyl)amino]-5-($C_{1-2}$alkoxy)phenyl.

7. A compound according to claim 6 wherein K'''' is 2-methyl-4-[N,N-di-($C_{2-4}$alkyl)amino]phenyl.

8. A compound according to claim 6 wherein K'''' is 2-acetamido-4-[N,N-di-($C_{2-3}$alkyl)amino]phenyl.

9. A compound according to claim 6 wherein K'''' is 2-acetamido-4-[N,N-di-($C_{2-4}$alkyl)amino]-5-($C_{1-2}$alkoxy)phenyl.

10. The compound according to claim 6 wherein K'''' is 2-methyl-4-(N-ethyl-N-γ-ethoxycarbonylpropylamino)phenyl.

11. The compound according to claim 6 wherein K'''' is 2-methyl-4-(N-ethyl-N-γ-phenoxypropylamino)phenyl.

12. The compound according to claim 6 wherein K'''' is 2-acetamido-4-(N-β-ethoxycarbonylethylamino)-5-ethoxyphenyl.

13. The compound according to claim 4 having the formula

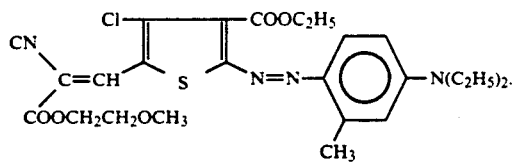

14. The compound according to claim 8 having the formula

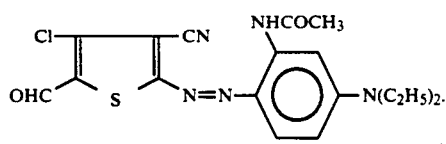

15. The compound according to claim 5 having the formula

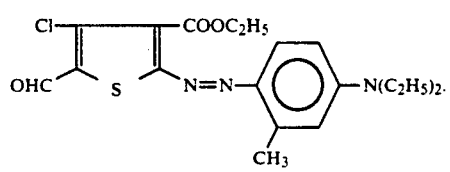

16. The compound according to claim 5 having the formula

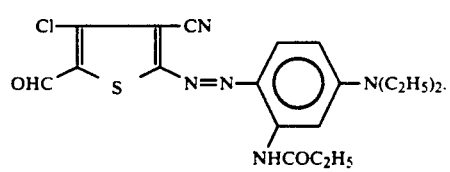

17. The compound according to claim 4 having the formula

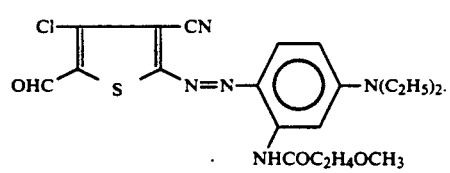

18. A process for dyeing a substrate comprising applying to a substrate a compound according to claim 1.

19. A substrate dyed with a compound according to claim 1.

* * * * *